(12) United States Patent
John

(10) Patent No.: US 10,682,153 B2
(45) Date of Patent: *Jun. 16, 2020

(54) FLAT OBJECT GRASPER

(71) Applicant: United States Endoscopy Group, Inc., Mentor, OH (US)

(72) Inventor: Keith R. John, Chardon, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 200 days.

This patent is subject to a terminal disclaimer.

(21) Appl. No.: 15/714,381

(22) Filed: Sep. 25, 2017

(65) Prior Publication Data

US 2018/0008299 A1 Jan. 11, 2018

Related U.S. Application Data

(63) Continuation of application No. 14/703,846, filed on May 4, 2015, now Pat. No. 9,770,254.

(Continued)

(51) Int. Cl.
*A61B 17/29* (2006.01)
*A61B 17/00* (2006.01)
(Continued)

(52) U.S. Cl.
CPC ........ *A61B 17/29* (2013.01); *A61B 17/00234* (2013.01); *A61B 17/0467* (2013.01); *A61B 17/320016* (2013.01); *A61B 17/0469* (2013.01); *A61B 17/3201* (2013.01); *A61B 2017/00296* (2013.01); *A61B 2017/00438* (2013.01); *A61B 2017/2905* (2013.01); *A61B 2017/2926* (2013.01); *A61B 2017/2932* (2013.01); *A61B 2017/2939* (2013.01); *A61B 2017/2947* (2013.01); *A61B 2017/320044* (2013.01)

(58) Field of Classification Search
CPC ................ A61B 17/29; A61B 17/0467; A61B 17/320016

See application file for complete search history.

(56) References Cited

U.S. PATENT DOCUMENTS

| | | | |
|---|---|---|---|
| 4,763,668 A * | 8/1988 | Macek | A61B 10/06 600/564 |
| 5,228,451 A | 7/1993 | Bales et al. | |

(Continued)

OTHER PUBLICATIONS

Office Action from U.S. Appl. No. 14/703,846 dated Feb. 1, 2017.

(Continued)

*Primary Examiner* — Richard G Louis
(74) *Attorney, Agent, or Firm* — Calfee, Halter & Griswold LLP

(57) ABSTRACT

A rotatable jaw device for use with an endoscope and method of using a rotatable jaw device. The device includes a fork, and two jaws pivotally mounted to the fork. The jaws are movable between a predetermined closed position and a predetermined open position. At least one jaw has at least one protrusion on a surface of the jaw. The at least one protrusion prohibits movement of the two jaws in the opening direction beyond the predetermined open position. One jaw may have an elongated center void defined by twin jaw extensions, and the other jaw may rotate within the elongated center void when the two jaws move toward the predetermined closed position.

12 Claims, 6 Drawing Sheets

Related U.S. Application Data

(60) Provisional application No. 61/987,961, filed on May 2, 2014.

(51) Int. Cl.
*A61B 17/04* (2006.01)
*A61B 17/32* (2006.01)
*A61B 17/3201* (2006.01)

(56) References Cited

U.S. PATENT DOCUMENTS

| | | | |
|---|---|---|---|
| 5,312,434 A | | 5/1994 | Crainrich |
| 5,366,467 A | | 11/1994 | Lynch et al. |
| 5,486,189 A | | 1/1996 | Mudry |
| 5,569,243 A | | 10/1996 | Kortenbach et al. |
| 5,893,874 A | | 4/1999 | Bourque |
| 2003/0069598 A1 | * | 4/2003 | Miser ............ A61B 17/29 606/205 |
| 2006/0271101 A1 | * | 11/2006 | Saadat ............ A61B 17/0469 606/205 |
| 2007/0049966 A1 | * | 3/2007 | Bonadio ............ A61B 17/00234 606/206 |
| 2007/0072466 A1 | * | 3/2007 | Miyamoto ............ A61B 17/29 439/188 |
| 2008/0243175 A1 | * | 10/2008 | Moore ............ A61B 17/7083 606/206 |
| 2009/0209946 A1 | * | 8/2009 | Swayze ............ A61B 17/07207 606/1 |
| 2010/0131005 A1 | * | 5/2010 | Conlon ............ A61B 17/29 606/207 |
| 2016/0066947 A1 | | 3/2016 | Mitelberg et al. |

OTHER PUBLICATIONS

Office Action from U.S. Appl. No. 14/703,841 dated Mar. 24, 2017.
Amendment from U.S. Appl. No. 14/703,841 dated Jun. 26, 2017.
Amendment from U.S. Appl. No. 14/703,846 dated May 1, 2017.
Notice of Allowance from U.S. Appl. No. 14/703,846 dated May 24, 2017.
Notice of Allowance from U.S. Appl. No. 14/703,841 dated Jul. 18, 2017.
Office Action from U.S. Appl. No. 15/818,030 dated Jul. 23, 2019.
Office Action from U.S. Appl. No. 15/818,030 dated Nov. 5, 2019.
Office Action from U.S. Appl. No. 15/818,030 dated Mar. 9, 2020.

* cited by examiner

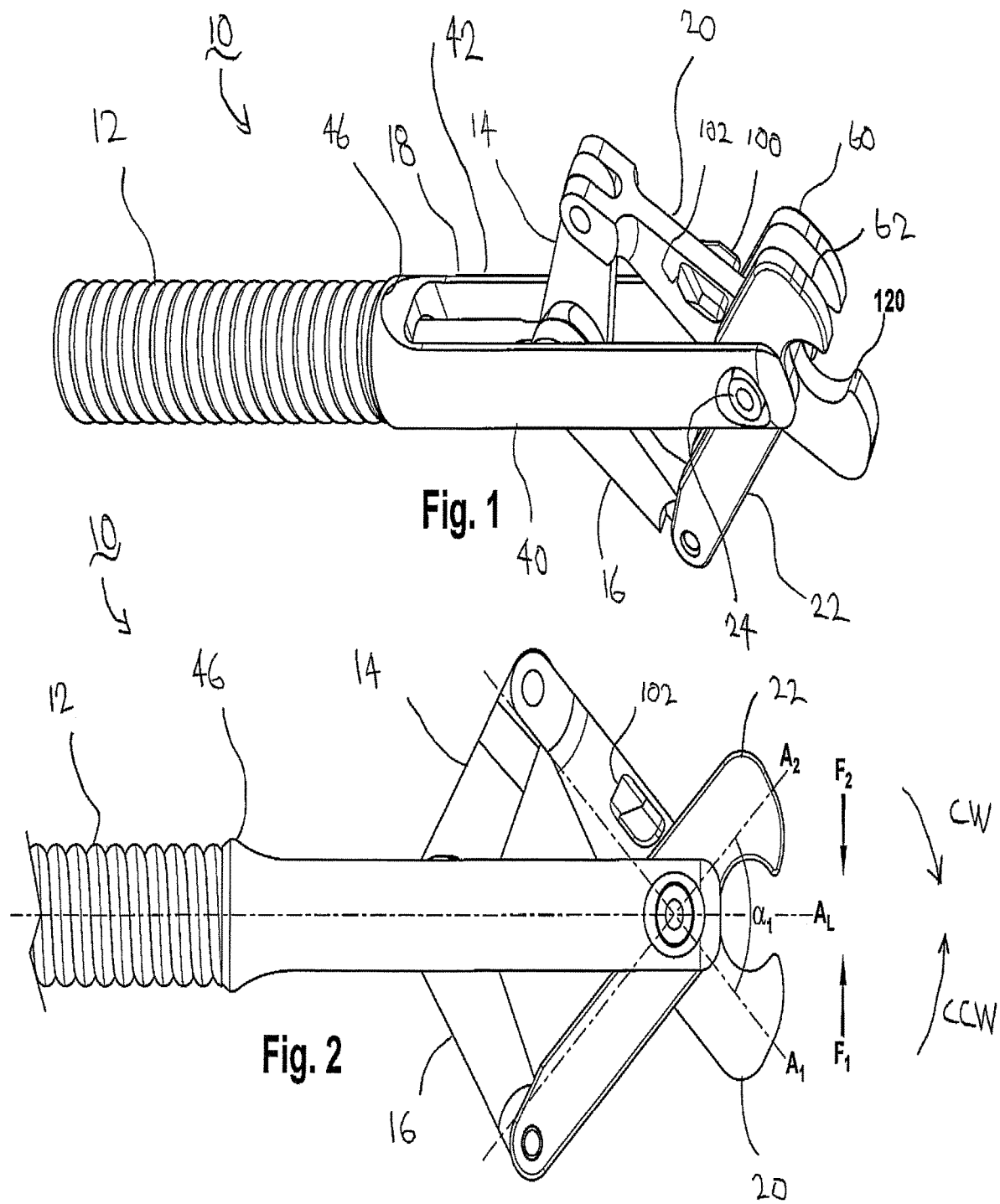

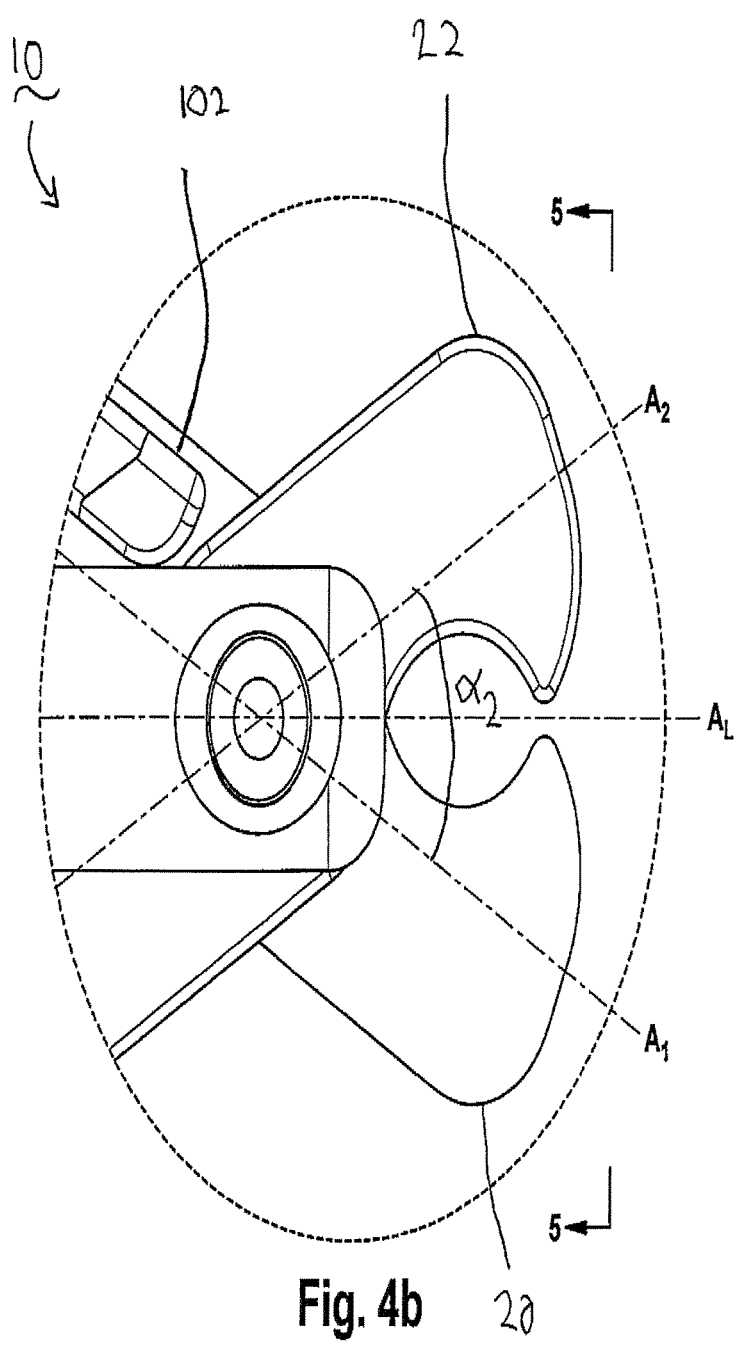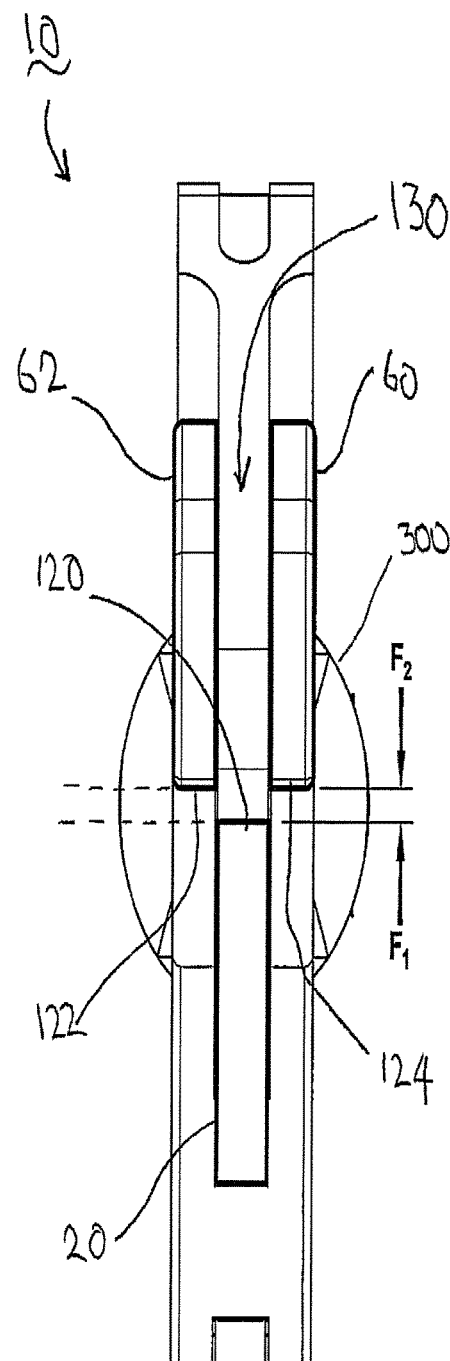
Fig. 4b
Fig. 5

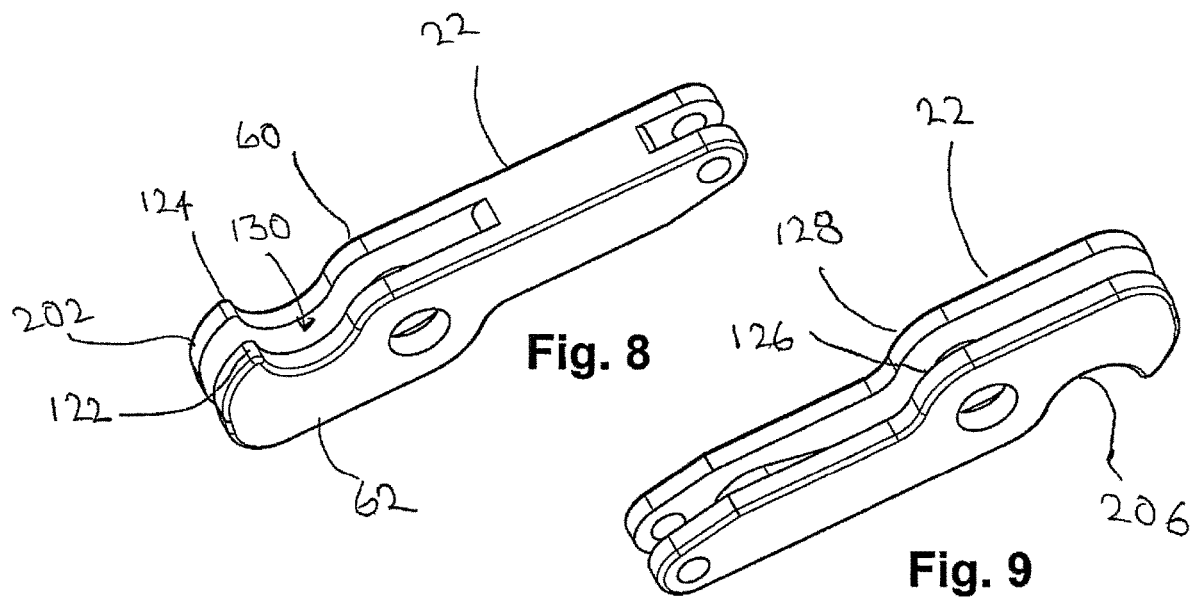
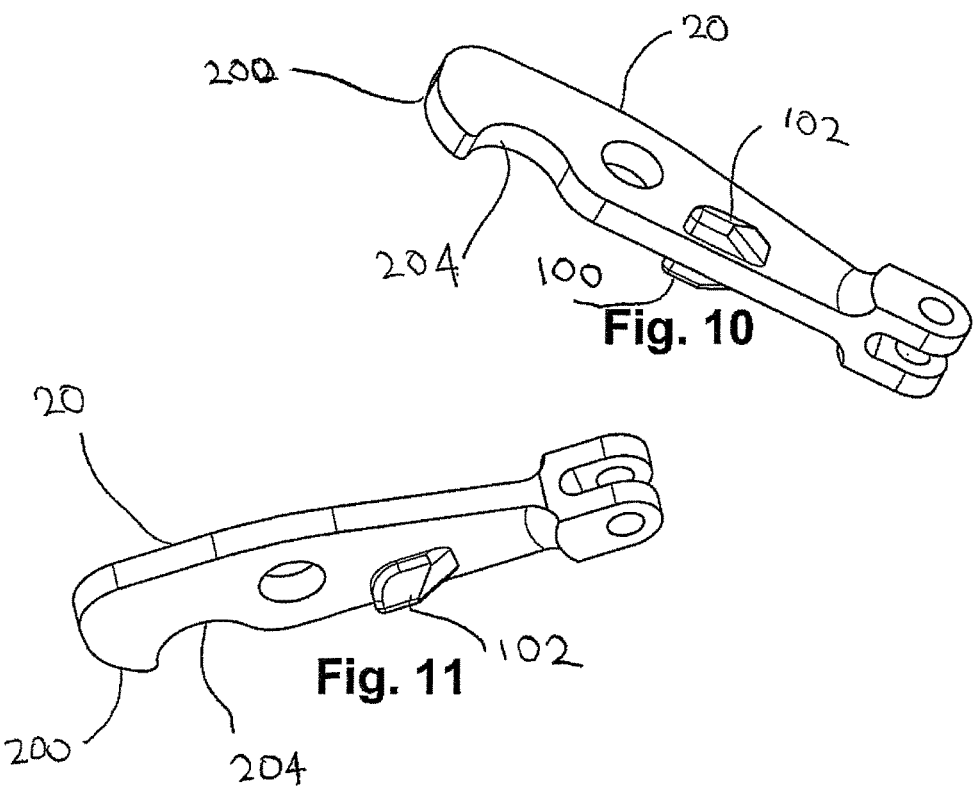

FLAT OBJECT GRASPER

CROSS-REFERENCE TO RELATED APPLICATIONS

This application claims the benefit of and priority to U.S. patent application Ser. No. 14/703,846, entitled FLAT OBJECT GRASPER filed on May 4, 2015, and U.S. Provisional Patent Application Ser. No. 61/987,961, entitled ENDOSCOPIC SUTURE CUTTER filed on May 2, 2014, the entire disclosures of which are incorporated herein by reference, to the extent that they are not conflicting with the present application.

BACKGROUND

Endoscopes are well-known in the medical arts and are commonly used for numerous medical procedures. Many such procedures require an endoscopic tool which is placed within an instrument channel in an endoscope. One type of endoscopic tool is a device with two rotatable jaws. One type of procedure using a device with two rotatable jaws is removing sutures from the inside of a human subject, such as from the wall or the gastrointestinal tract. One conventional technique for removing sutures is using a cutting tool in an endoscopic procedure. Another procedure is removing foreign objects from inside the body by the use of a grasping tool.

Known grasping devices in the art have one or two jaws which pivot relative to a base. The jaw may be pivoted by a user operating a handle at a proximal end of the device and at a proximal location outside of the endoscope. Serious complications may arise during grasping removal procedures when the jaws of the grasper become stuck, either in an over-closed position or in an over-opened position. Further, the grasper may not firmly secure the object when first making contact with it, and consequently the object may not be secured with the jaws long enough to be removed from the patient.

SUMMARY

The present application describes a rotatable jaw device for use with an endoscope.

In an exemplary embodiment, a rotatable jaw includes a fork, and two jaws pivotally mounted to the fork. The jaws are movable between a predetermined closed position and a predetermined open position. The jaws may have one or more protrusions on a jaw surface which may limit rotational movement of the jaws.

Further features and advantages of the invention will become apparent from the following detailed description made with reference to the accompanying drawings.

BRIEF DESCRIPTION OF THE DRAWINGS

Features and advantages of the general inventive concepts will become apparent from the following detailed description made with reference to the accompanying drawings.

FIG. 1 is a side perspective view of the distal end of an endoscopic grasping device, with the jaws shown in an open position;

FIG. 2 is a side view of the distal end of the grasping device of FIG. 1, with the jaws shown in an open position;

FIG. 4b is an enlarged view of the area designated in FIG. 4a;

FIG. 5 is a front view of the distal end of the grasping device of FIG. 1, with the jaws shown in a grasping position;

FIG. 8 is a top perspective view of the second jaw of the grasping device of FIG. 1;

FIG. 9 is a bottom perspective view of the jaw of FIG. 8;

FIG. 10 is a top perspective view of the first jaw of the grasping device of FIG. 1;

FIG. 11 is a bottom perspective view of the jaw of FIG. 10; and

DETAILED DESCRIPTION

Figure 3:
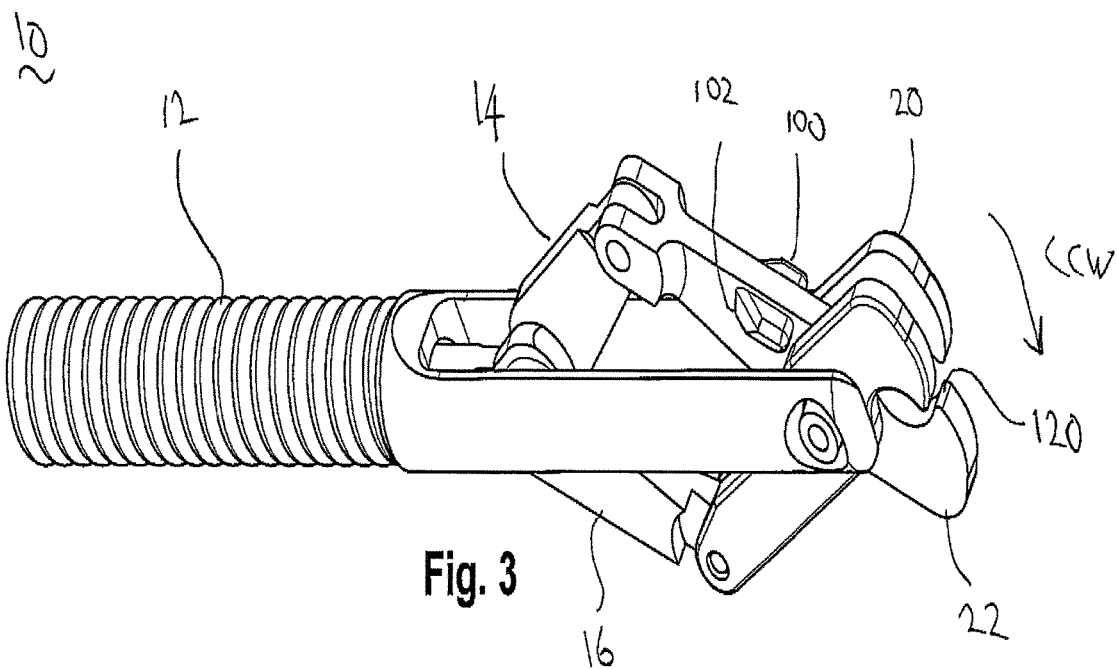
FIG. 3 is a side perspective view of the distal end of the grasping device of FIG. 1, with the jaws shown in a grasping position.

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

In discussing the invention, the terms "proximal" and "distal" are often used. These terms are used to describe a position or a direction with reference to the operator of the tool. For example, the proximal position or proximal direction is toward the user or operator of the tool, and the distal position or direction is away from the user or operator of the tool, i.e., position or direction toward the suture.

Removal of foreign objects by an endoscopic procedure is a well-known medical procedure. The difficulty in removing the objection can be a function of the shape and/or size of the object. For example, flat objects, such as a penny or a poker disc, can be difficult to remove because of the skill level required to grasp and secure the flat object with a conventional grasping device.

In addition, several limitations exist with conventional grasping devices and grasping techniques. Despite careful use, the handle slider may be moved too hard or too far in the opening direction, thus causing the jaws of a grasping device to be rotated to a so-called "over-opened" position. In other words, the jaws may be rotated beyond a desired open position and become stuck, so that the jaws may not be closed by sliding the handle. The jaws in this position may be locked in a perpendicular, or just past perpendicular, position relative to the base. This position is sometimes referred to in the art as the "T-bone" position. When the jaws reach the T-bone position, or any undesired open position and become stuck, the tool can no longer be removed through the channel of the endoscope. This condition may require surgery from outside the body and through the gastrointestinal wall, which severely complicates an otherwise relatively routine endoscopic procedure.

The jaws of a conventional cutter may be rotated to a so-called "over-closed" position. In other words, despite careful use, the slider may be moved too hard or too far in the closing direction, thus causing the jaws of a grasping device to be rotated beyond a desired closed position and become stuck, so that the jaws may not be opened by sliding the handle. The jaws in this position may be locked in just past parallel position relative to the base. When a jaw reaches an undesired closed position and becomes stuck, the tool can no longer be opened and must be removed from the endoscope. This condition may require manual opening of the jaws or more likely a new and sterile grasping device will be required. This condition adds time and cost to the procedure.

Various solutions to prevent the over-opened and over-closed condition have been considered in the art. One considered solution uses a bump or stopper on the inside surface of the jaw. A bump in this location on a jaw would block further opening of the pair of jaws when the bump intersects with the other jaw, and block further closing of the pair of jaws when the bump intersects with the other jaw. However, a bump on the inside surface of the jaw adds complexity to the requirement of sharpening the blade, such as for example, by eliminating any automated side-to-side sharpening of the inside surface.

The present invention is directed to an endoscopic tool which includes two jaws which are each pivotally mounted to a fork. At least one jaw is advantageously shaped to prohibit over-opening beyond a desired position.

The present invention may be practiced as various types of a two-jaw device, such as a grasping device or endoscopic suture cutter. The device may include a handle, a spring sheath catheter, two linkage control arms, a fork, and two jaws pivotally mounted to the fork. The jaws may be manipulated between a desired open position and a desired closed position. A protrusion, or bump, on the outside surface of one jaw prohibits the jaws to be opened beyond the desired open position. Thus, an over-opened condition is prohibited.

In an exemplary embodiment of the invention, a rotatable jaw device for use with an endoscope is disclosed. The device includes a fork and two jaws pivotally mounted to the fork. The jaws are movable between a predetermined closed position and a predetermined open position. At least one jaw has at least one protrusion on a surface of the jaw. The at least one protrusion prohibits movement of the two jaws in the opening direction beyond the predetermined open position.

In another exemplary embodiment of the invention, a grasping device for use with an endoscope is disclosed. The grasping device includes a fork, and a first jaw and a second jaw. The first jaw and the second jaw are pivotally mounted to the fork and rotatable between a predetermined closed position and a predetermined open position. The first jaw has at least one protrusion on a surface of the jaw. The at least one protrusion contacts the second jaw to prohibit movement of the two jaws in the opening direction beyond the predetermined open position.

In another exemplary embodiment of the invention, a grasping device for use with an endoscope is disclosed. The grasping device includes a body, a handle mounted to and movable relative to the body, a conduit having a first end fixed to the body and a second end, the conduit defining a passage and an opening at the second end, a fork having two prongs and attached to the distal end of the conduit, a first jaw and a second jaw, pivotally mounted to the fork within the two prongs, and dependently movable between a predetermined closed position and a predetermined open position, and a first linkage arm attached to a proximal end of the first jaw, and a second linkage arm attached to a proximal end of the second jaw. The jaws are rotatable between the predetermined closed position and the predetermined open position by operation of the handle. The first jaw has at least one protrusion on a surface of the jaw and the second jaw has an elongated center void defined by twin jaw extensions. The first jaw is positioned within the elongated center void when the two jaws are in the predetermined closed position. The at least one protrusion on a surface of a first jaw prohibits movement of the two jaws in the opening direction beyond the predetermined open position.

The protrusion which prohibits an over-opened condition has other benefits. By giving a physician confidence against an over-opened condition, the physician may apply pressure in the opening direction to hold the jaws firmly in the maximum open condition. Thus, the physician can be confident in maneuvering the grasping device around the exterior of the targeted flat object.

Referring now to the drawings, FIG. 1 is a front perspective view of the distal end of an endoscopic suture cutter 10. The cutter 10 includes a handle, a spring sheath catheter 12, two linkage control arms 14, 16, a fork 18, and two jaws 20, 22 pivotally mounted to the fork 18 by a rivet 24. Movement of the control arms 14, 16 in the distal direction closes the jaws 20, 22 and movement of the control arms 14, 16 in the proximal direction open the jaws 20, 22. Movement of the control arms 14, 16 is controlled by manipulation of the handle by a user. The way in which the jaws are secured together, and to the fork, may be modified in the practice of this invention.

Figure 12:
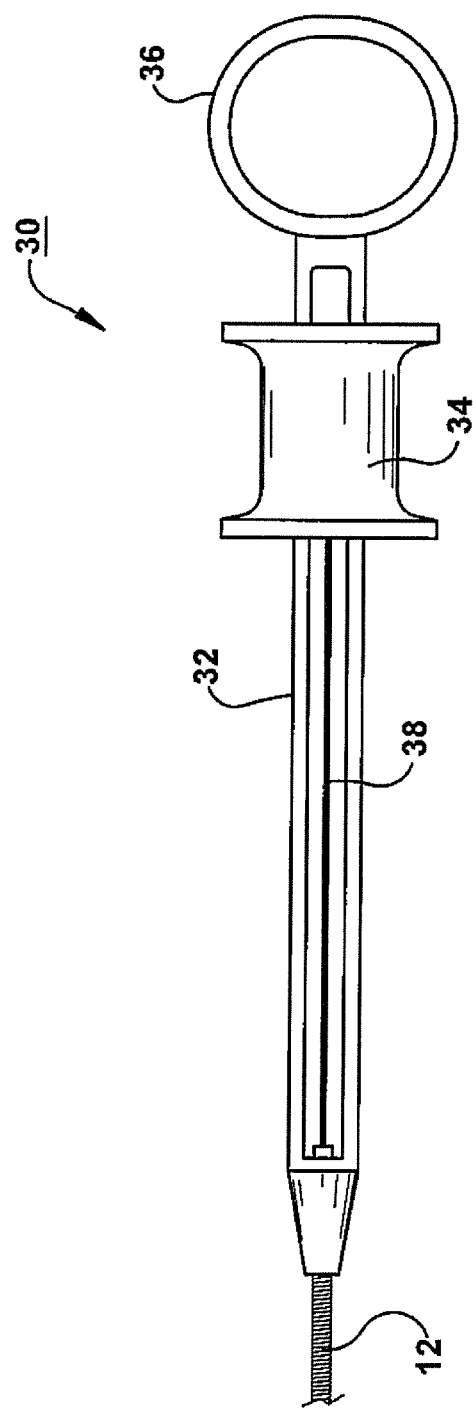
FIG. 12 is a front view of the proximal end of the grasping device of FIG. 1, showing a handle assembly.

Referring now to FIG. 12, a front view of the proximal end of the endoscopic grasping device 10 is shown. A handle assembly 30 is shown and includes a base 32 and a slider 34. The handle is used to transfer the linear motion of the slider to open and close the jaws on the distal end. In operation of the handle 30, a user may insert a thumb from one hand into a ring 36 and rest several fingers from the same hand on the slider 34. Movement of the slider 34 relative to the base 32 causes movement of a link 38. The link 38 may be attached directly or indirectly to the control arms 14, 16 within the spring sheath catheter 12. The user may open the jaws by actuating the handle slider and moving it in the proximal direction. The user may grasp a flat object with the distal end of the jaws 20, 22 and close the jaws by moving the slider in the distal direction. It should be apparent to one skilled in the art that the design and operation of the handle assembly and the link to the control arms may vary in the practice of this invention.

Referring again to FIG. 1, the spring sheath catheter 12 runs the length of the device 10 from the fork 18 to the handle 30. The spring sheath catheter 12 is formed of a coil wire and can be a variety of shapes, such as for example, a circular cross section or a rectangular cross section. The spring sheath may be PTFE (Teflon) coated or a heat shrink coated on the outside. The diameter of the spring sheath catheter 12 may vary in diameter, such as for example, the outside diameter range may be 0.080 to 0.100 cm. The length of the sheath is long enough to allow reasonable length beyond the proximal end and beyond the distal end of an endoscope, such as for example, the total length of the cutter 10 may be 165 cm.

The fork provides a mounting location for the jaws. As shown in FIG. 1, the fork 18 includes two tangs 40, 42 protruding distally from a base 46. Each tang defines a mounting aperture through which the rivet 24 is placed. A space between the tangs allow for pivoting movement of the jaws 20, 22 in either rotational direction. Discussed herein in greater detail, each fork defines a recess 50 which is cooperatively shaped to allow insertion of a bump on a jaw.

A side perspective view of the distal end of the grasper device 10 is shown in FIG. 2. In this Figure, the jaws 20, 22 are shown in an open position. Specifically, the jaws 20, 22 are shown in a predetermined open position. The embodiment illustrated prohibits opening of the jaws from opening beyond this position. For example, the jaws 20, 22 are rotated α degrees apart from each other. In one embodiment, the jaws are rotated a total of no more than 90 degrees away from each other from each other. This embodiment is shown for exemplary purposes only, and the device 10 may be modified in the practice of the invention to allow the maximum opened condition to be more or less the amount shown relative to the longitudinal axis $A_L$ of the device.

As shown in FIG. 2, two protrusions 100, 102 are on opposite side surfaces of the first jaw 20. When the jaws reach the predetermined open position, the protrusions 100, 102 each contact the top surface of the second jaw 22. This contact prohibits additional rotation of the distal end of the second jaw 22 in the counterclockwise CCW direction.

The second jaw 22 has two twin jaw protrusions 60, 62. The twin protrusions 60, 62 are identical in shape and size. Further structure of the second jaw 22 is discussed herein.

The grasping device may be manually rotated to a preferred grasping position between the predetermined open position and the predetermined closed position. In this preferred grasping position, the jaws reach contact with a targeted flat object and a contact surface of each jaw is planar, and in a parallel orientation with the contact surface of the other jaw. As such, the first jaw and the second jaw act to grip the object like a vise, with all forces acting perpendicular to the upper surface and lower surface of the targeted flat object. The grasping device is shown in an exemplary preferred grasping position in FIGS. 3-5. These figures will now be discussed in detail.

Figure 4A:
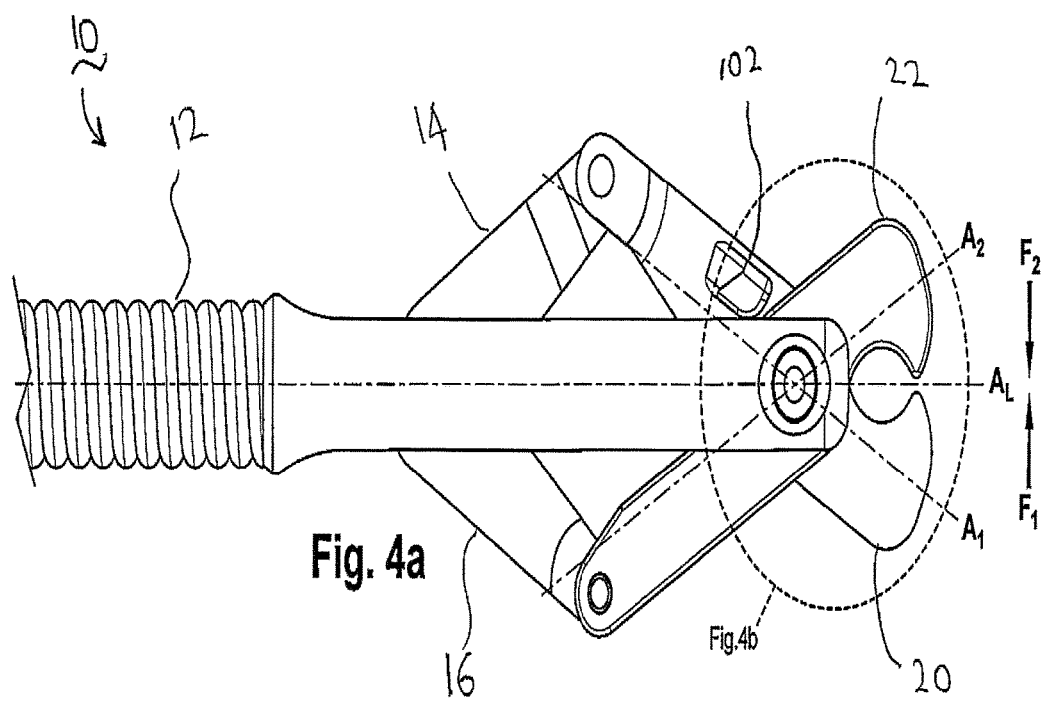
FIG. 4a is a side view of the distal end of the grasping device of FIG. 1, with the jaws shown in a grasping position.

Referring now to FIG. 3, a side perspective view of the distal end of the grasping device 10 is shown. In this figure, the jaws 20, 22 are shown in a preferred grasping position. A similar view is shown in FIGS. 4a and 4b. FIG. 5 shows the jaws 20, 22 in a preferred grasping position from a front view. As shown, the planar contact surface 120 of jaw 20 is shown to be parallel to the planar contact surfaces 122, 124 of the twin jaw extensions 60, 62, respectively, of the second jaw 22. Further as shown, the planar contact surface 120 is moving downward in a direction $F_2$ at the point of contact and the planar contact surfaces 122, 124 are moving downward in a direction $F_1$ at the point of contact. This orientation prohibits an angled contact surface, which often forces the grasped device to escape out of the jaws in the distal direction. Further, FIG. 5 is a clear showing of the void 130 between the twin jaw extensions 60, 62 in which the first jaw 20 rotates when in or near the closed position.

FIG. 5 illustrates an advantageous mechanical feature of the grasping device 10. When designing an endoscopic device, the device must be constructed to fit into an endoscopic channel. For example, the front view of FIG. 5 shows the outer circumferential surface 300 of the grasping device 10. This space is relatively small, and many conventional devices designed to work in this space offer very limited leverage. By a device being limited to this size, the jaws often are arranged in an orientation which only affords the device limited leverage for grasping an object. Thus, a user of a grasping device may be able to grasp a razor blade, or a similar flat object, but the grasping device will lack leverage and the user will not be able to maintain a grip on the flat object when the user attempts to withdraw the flat object from the patient.

The inventive arrangement of the two jaws 20, 22 offers increased leverage over a conventional grasping device. As best seen in FIG. 5, the first jaw 20 passes inside of the second jaw 22 in the closed position. However, in a grasping position, as is shown in FIGS. 4B and 5, the jaws 20, 22, are at a relatively large angle $α_2$ to each other when the jaws are in the grasping position. In this position, a relatively large amount of leverage is offered within the small device space. Further, as seen in FIGS. 8-11, the rotation point of the two jaws 20, 22 is well within the distal half of the jaw. In other words, the pivot point of the first jaw and the pivot point of the second jaw is located at a point which is closer to the distal end of the jaw than the proximal end of the jaw.

Figure 6:
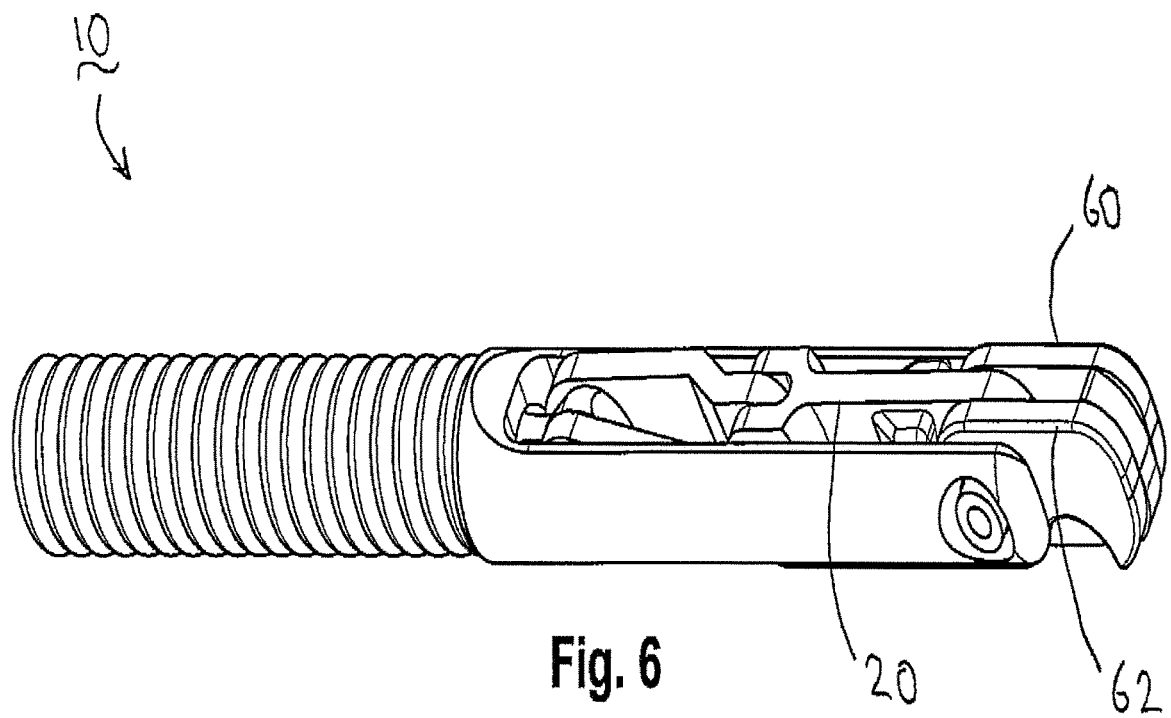
FIG. 6 is a side perspective view of the grasping device of FIG. 1, with the jaws shown in a closed position.
Figure 7:
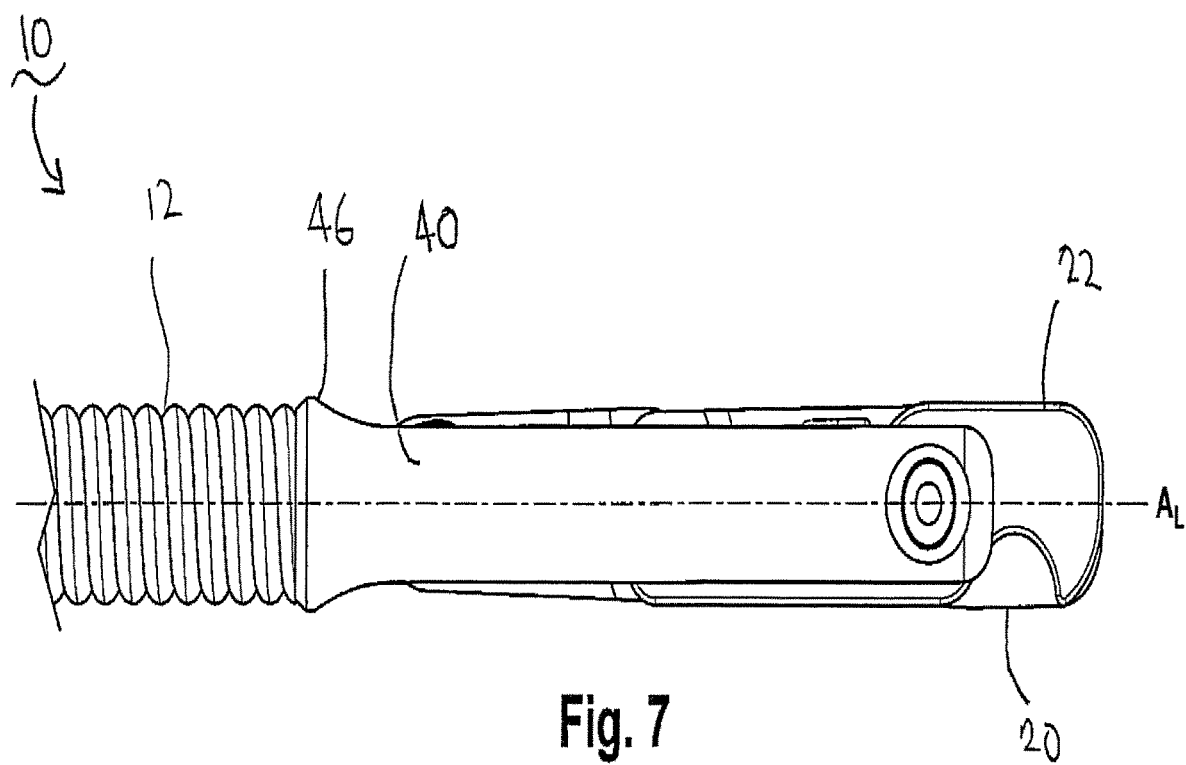
FIG. 7 is a side view of the distal end of the grasping device of FIG. 1, with the jaws shown in a closed position.

A view of the jaws 20, 22 in a predetermined closed position is shown in FIGS. 6 and 7. The embodiment illustrated prohibits closing of the jaws beyond this position. For example, the jaws 20, 22 are rotated to about a parallel position relative the longitudinal axis $A_L$ of the fork. This embodiment is shown for exemplary purposes only, and the grasping device 10 may be modified in the practice of the invention to allow the maximum closed condition to be more or less than 0 degrees relative to the longitudinal axis $L_1$ of the fork.

The shape of the first jaw and the second jaw are illustrated in FIGS. 8-11. FIGS. 8 and 9 show the second jaw 22. The second jaw 22 has several advantageous features.

The distal end 202 of the jaw 20 is configured in a convex, parrot-like shape. All surfaces of the distal end 200 are rounded. With these rounded surfaces, a user is less likely to inadvertently scrape, cut or otherwise damage any gastrointestinal wall tissue during the grasping and removal procedure. Further, the overall shape of the concave, top surface 206 allows for the second jaw 20 to be used by the user to snag imbedded flat objects. The shape of the distal end illustrated is for exemplary purposes and may vary in other embodiments of the invention.

The second jaw 22 is made to be a unique shape and size relative to the first jaw 20. The twin extension jaws 122, 124 define a void 130, as best seen in FIG. 8. The bottom surface of each twin extension 60, 62 may be contoured and cooperatively shaped to engage the protrusions 100, 102 on the first jaw 20.

As discussed herein, the first jaw has a unique shape relative to the second jaw. For discussion purposes, the first jaw 20 is shown in various views in FIGS. 10-11. The first jaw 20 has several advantageous features. The distal end 200 of the jaw 20 is configured in a convex, parrot-like shape. All surfaces of the distal end 200 are rounded. With these rounded surfaces, a user is less likely to inadvertently scrape, cut or otherwise damage any gastrointestinal wall tissue during the suture cutting and removal procedure. Further, the overall shape of the concave, top surface 204 allows for the first jaw 20 to be used by the user to snag imbedded flat objects. The shape of the distal end illustrated is for exemplary purposes and may vary in other embodiments of the invention.

As discussed herein, the first jaw includes two protrusions 100. The bump as shown defines a curved surface extending away from the body of the jaw. In the embodiment shown, the two protrusions are identical in size, and have the same shape in a mirror orientation. The height and shape of the protrusion may vary in the practice of the invention.

A method of operation of the grasping device as described herein is also inherent to the present invention.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A method of grasping an object with an endoscopic tool, comprising the steps of:
   inserting an endoscopic tool having an end effector into a cavity;
   moving an end effector from a predetermined closed position to a predetermined open position,
      wherein the end effector comprises a first jaw and a second jaw, the first and second jaw each attached to a fork at a distal end of the endoscopic tool, wherein the second jaw has an elongated center void defined by twin jaw extensions, and the first jaw is rotatable within the elongated center void;
   stopping the first and second jaw from opening farther than the predetermined open position by having at least one protrusion on each side of the first jaw, such that each of the protrusions contacts one of the twin jaw extensions of the second jaw when the jaws reach the predetermined open position;
   maneuvering the end effector around the exterior of a targeted object; and
   moving the end effector from the predetermined open position to the predetermined closed position, such that at least one flat grasping surface on each of the jaws contacts the targeted object.

2. The method of claim 1, wherein the first and second jaws in the predetermined open position are rotated no more than 90 degrees from each other.

3. The method of claim 1, wherein the first and second jaws in the predetermined closed position are side-by-side and rotated zero degrees relative to each other.

4. The method of claim 1, further comprising moving the jaws past an intermediate position, between the predetermined open position and the predetermined closed position, wherein at the intermediate position the at least one flat grasping surface of each jaw are parallel to each other.

5. The method of claim 1, wherein the step of opening the jaws comprises moving a slider in a proximal direction relative to a handle base.

6. The method of claim 5 wherein the step of closing the jaws comprises moving the slider in a distal direction relative to the handle base.

7. The method of claim 1, further comprising the steps of removing the targeted object by:
   moving the end effector away with the targeted object held in between the at least one grasping surface of each of the jaws; and
   withdrawing the endoscopic tool from the cavity.

8. A grasping device for use with an endoscope, the device comprising:
   a fork;
   a first control arm comprising a proximal end and a distal end, wherein the proximal end is connected to the fork;
   a second control arm comprising a proximal end and a distal end, wherein the proximal end is connected to the fork;
   a first jaw comprising a proximal end and a distal end, wherein the proximal end is rotatably connected to a distal end of the first control arm;
   a second jaw comprising twin jaw extensions defining an elongated center void, a proximal end, and a distal end, wherein the proximal end is rotatably connected to a distal end of the second control arm;
   wherein the first and second jaw are rotatable relative to each other between a predetermined open position and a predetermined closed position at a rotation point, the first jaw positioned in the elongated center void when in the predetermined closed position;

wherein the first jaw comprises at least one protrusion on each side; and wherein the rotation point is located closer to the distal ends of the jaws than the proximal ends of the jaws.

9. The device of claim 8 wherein the first and second control arms are connected to the fork midway between a proximal end and a distal end of the fork.

10. The device of claim 8 wherein the rotation point is located at the distal end of the fork.

11. The device of claim 8 wherein the second jaw has no protrusions which contact the first jaw to prohibit movement of the two jaws beyond a predetermined open position.

12. The device of claim 8 wherein the fork is attached to a distal end of a spring sheath catheter, wherein the proximal end of the sprig sheath catheter is connected to a handle assembly.

* * * * *